United States Patent
Takei et al.

(10) Patent No.: US 7,022,124 B2
(45) Date of Patent: Apr. 4, 2006

(54) SURGICAL INSTRUMENT

(75) Inventors: Tsunenori Takei, c/o Asahi Kogaku Kogyo Kabushiki Kaisha 36-9, Maenocho 2-chome, Itabashi-ku, Tokyo (JP); Yukio Taniguchi, Saitama-ken (JP); Yoshie Tominaga, Saitama-ken (JP)

(73) Assignees: PENTAX Corporation, Tokyo (JP); Tsunenori Takei, Nagano-ken (JP)

( * ) Notice: Subject to any disclaimer, the term of this patent is extended or adjusted under 35 U.S.C. 154(b) by 3 days.

(21) Appl. No.: 10/119,779

(22) Filed: Apr. 11, 2002

(65) Prior Publication Data
US 2002/0151903 A1 Oct. 17, 2002

(30) Foreign Application Priority Data
Apr. 12, 2001 (JP) .......................... 2001-114426

(51) Int. Cl.
*A61B 17/58* (2006.01)
*A61F 2/00* (2006.01)

(52) U.S. Cl. ..................................................... 606/99
(58) Field of Classification Search ............. 623/11.11, 623/13.12, 13.13, 13.14; 29/241, 278, 280; 606/53, 86, 96, 99, 104
See application file for complete search history.

(56) References Cited

U.S. PATENT DOCUMENTS

| | | | | |
|---|---|---|---|---|
| 2,379,629 A * | 7/1945 | Eweson | .................. | 294/1.2 |
| 4,405,314 A * | 9/1983 | Cope | ..................... | 604/510 |
| 4,738,255 A | 4/1988 | Goble et al. | | |
| 4,769,005 A * | 9/1988 | Ginsburg et al. | .......... | 604/510 |
| 4,950,270 A | 8/1990 | Bowman et al. | | |
| 5,139,499 A * | 8/1992 | Small et al. | .................. | 606/73 |
| 5,257,979 A * | 11/1993 | Jagpal | ........................ | 604/272 |
| 5,389,087 A * | 2/1995 | Miraki | ....................... | 604/247 |
| 5,411,506 A | 5/1995 | Goble et al. | | |
| 5,411,523 A | 5/1995 | Goble | | |
| 5,423,819 A * | 6/1995 | Small et al. | ................... | 606/73 |
| 5,470,334 A * | 11/1995 | Ross et al. | ..................... | 606/72 |
| 5,665,086 A | 9/1997 | Itoman et al. | | |
| 5,731,087 A * | 3/1998 | Fan et al. | .................... | 428/412 |
| 5,807,236 A * | 9/1998 | Bacich et al. | ............... | 600/104 |
| 6,123,710 A * | 9/2000 | Pinczewski et al. | ........... | 606/73 |
| 6,179,809 B1 * | 1/2001 | Khairkhahan et al. | ... | 604/95.04 |
| 6,283,950 B1 * | 9/2001 | Appling | ....................... | 604/528 |
| 6,283,973 B1 | 9/2001 | Hubbard et al. | | |
| 6,306,177 B1 * | 10/2001 | Felt et al. | ................... | 623/23.6 |

(Continued)

FOREIGN PATENT DOCUMENTS

EP 0716832 A1 * 6/1996

(Continued)

*Primary Examiner*—Eduardo C. Robert
*Assistant Examiner*—Anu Ramana
(74) *Attorney, Agent, or Firm*—Greenblum & Bernstein P.L.C.

(57) ABSTRACT

There is provided a surgical instrument that includes an elongated body of which distal end is formed to press and drive a bone plug into a bone tunnel. The elongated body also has a guiding hole which is preferably formed along the longitudinal axis of the elongated body and in communication with a front opening formed at the distal end. The guiding hole is formed such that a guide wire can be inserted therein and extend out from the front opening. The guide wire is used to guide the bone plug towards the distal end of the surgical instrument and keep the bone plug there during driving it into the bone tunnel.

23 Claims, 16 Drawing Sheets

U.S. PATENT DOCUMENTS

Figure 1:
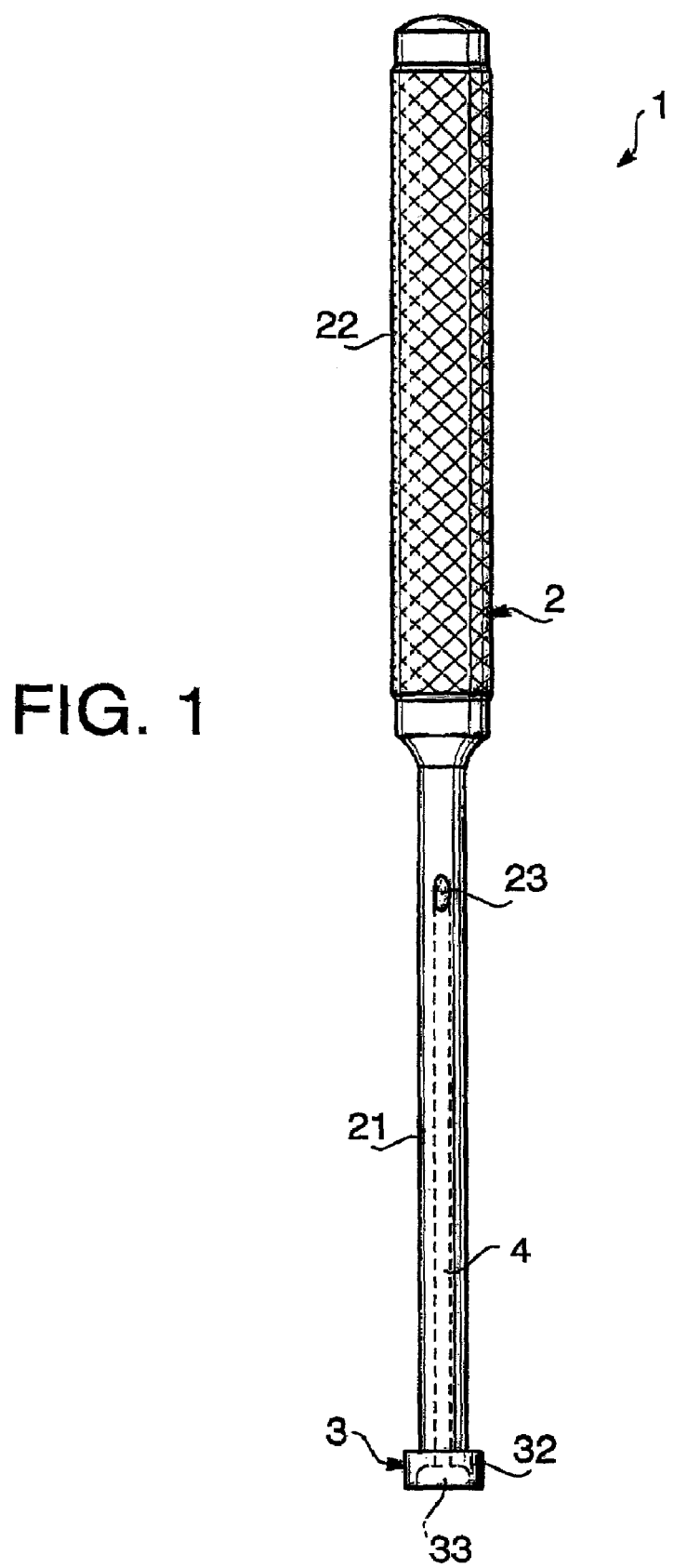

| | | | |
|---|---|---|---|
| 6,458,867 B1 * | 10/2002 | Wang et al. | 523/105 |
| 6,533,751 B1 * | 3/2003 | Cragg et al. | 604/93.01 |
| 2001/0029374 A1 * | 10/2001 | Kikuchi et al. | 606/61 |
| 2003/0028194 A1 | 2/2003 | St. Pierre et al. | |

FOREIGN PATENT DOCUMENTS

| | | |
|---|---|---|
| GB | 2312376 | 10/1997 |
| JP | 9-10245 | 1/1997 |
| WO | 89/01767 | 3/1989 |

* cited by examiner

SURGICAL INSTRUMENT

BACKGROUND OF THE INVENTION

The present invention relates to a surgical instrument, in particular, a surgical instrument for driving a bone plug into a hole formed in a bone for securing a ligament to the bone.

Artificial materials such as artificial ligaments and reinforcement meshes, or organic materials such as patella bone-tendon, hamstring muscle, and fascia lata are used for anterior cruciate ligament reconstructions. In early stages of the reconstruction surgery, the reconstruction ligament was fixed to the bone using an anchor bolt, for example. Today, the artificial ligament is fixed to the bone by inserting it into a hole formed in the bone, or bone tunnel, and then closing the bone tunnel with a bone chip, an interference screw, or an inner button. Such methods for fixing ligaments, however, do not provide a stable joint between the ligament and the bone, but the joint tends to become loose.

Recently, a new ligament fixing method is developed which provides more stable joint between the ligament and the bone by fixing the reconstruction ligament inserted in the bone tunnel by means of a bone plug. Japanese Patent application provisional publication H9-10245 discloses an example of such bone plugs made from bio-compatible material, such as calcium phosphate compound, formed in a hollow cylindrical shape having a hole extending along its center axis.

The bone plug is driven into the bone tunnel using a driving-instrument. Since the bone plug is driven into the bone inside a living body, e.g. inside the knee joint, the bone plug is hardly kept in a right attitude at a right position of the driving-instrument during the surgery, which in turn results in a rather long operation time. Accordingly, a surgical instrument is required that facilitates the plugging of the bone plug into the bone.

SUMMARY OF THE INVENTION

The present invention provides the advantages in that, in a surgical instrument, the bone plug can be easily kept at a right position of the surgical instrument during driving the bone plug into the bone tunnel and thus the surgeon can perform the operation smoothly.

According to embodiments of the invention, there is provided a surgical instrument that includes an elongated member of which a distal end is formed to press and drive a bone plug into a bone tunnel. The elongated member also has a guiding hole which is preferably formed along the longitudinal axis of the elongated member and in communication with a front opening formed at the distal end. The guiding hole is formed such that a guide wire, which may be an accessory of the surgical instrument in some embodiments of the invention, can be inserted therein and extend out from the front opening. The guide wire, extending out from the front opening, may be used to guide the bone plug towards the distal end of the surgical instrument and keep the bone plug there during driving it into the bone tunnel.

Optionally, the distal end includes a recess, possibly formed in a concave surface. Such recess contributes to stably receive the bone plug at the distal end of the surgical instrument during the operation.

In this above case, the front opening may be formed in the recess so that the bone plug will be received by the recess by traveling along the guide wire.

In some embodiments of the invention, a proximal end portion of the guiding hole is inclined against the longitudinal axis of the elongated member and forms a side opening at an outer peripheral surface of the elongated member such that the guide wire can be inserted into the guiding hole from the side hole. Preferably, the proximal portion of the guiding hole is inclined against the longitudinal axis of the elongated. member at an acute angle such that the guide wire extending out from the side opening does not incline towards the distal end of the elongated member and thereby hinder the operation.

One or both of the guiding hole and the guiding wire may be applied with a coating for decreasing friction between the guiding hole and the guide wire so that the guide wire moves smoothly through the guiding hole.

The elongated member may include a grip portion having an outer peripheral surface with small bumps and dips which prevent the hand of the surgeon from slipping over the elongated member.

In some embodiments of the invention, the elongated member includes a body and a detachable portion which includes the distal end of the elongated member and is detachably attached to the body. In such embodiments, the detachable portion of the elongated member can be changed, according to the type of the operation, for example, to one having a distal end of most appropriate shape and/or size for the operation.

The guide wire may include a wire to be inserted into the guiding hole from the side opening and extend out from the front opening, and a stopper fixed to the wire to prevent the wire from passing through the guide wire.

In some cases, the stopper is formed in a shape which is not able to be inserted into the guiding hole. For example, the stopper is a sphere having a diameter larger than the diameter of the side opening.

BRIEF DESCRIPTION OF THE ACCOMPANYING DRAWINGS

Figure 2:
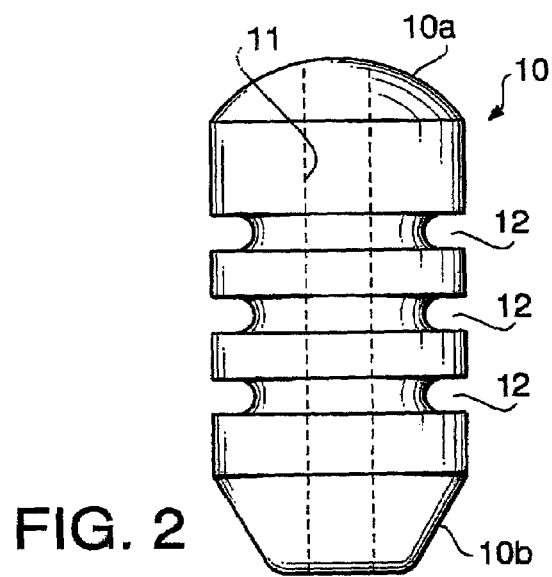

FIG. 1 shows a side view of the surgical instrument according to an embodiment of the invention, FIG. 2 shows a side view of a bone plug that is to be driven into a bone tunnel by the surgical instrument shown in FIG. 1

Figure 3:
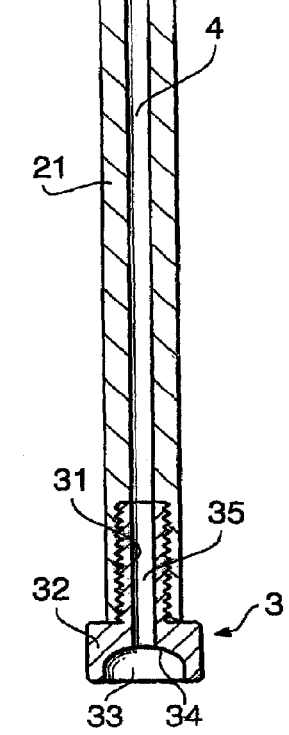
Figure 4:
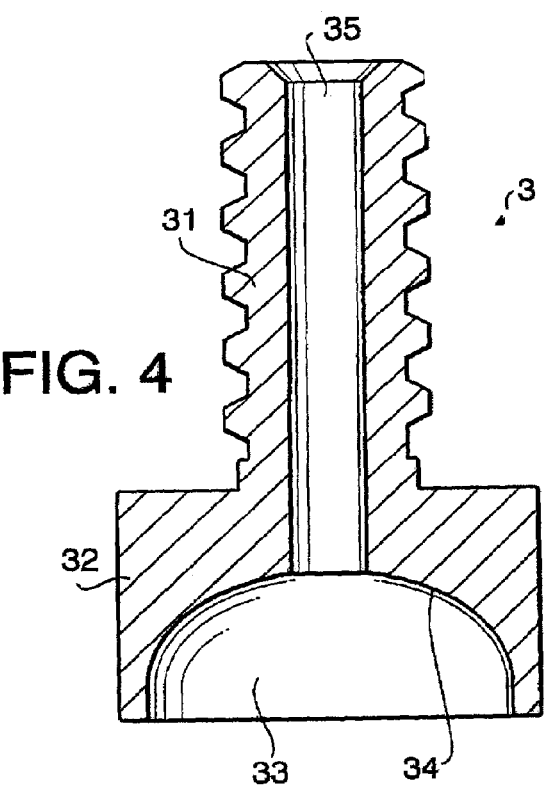
Figure 5:
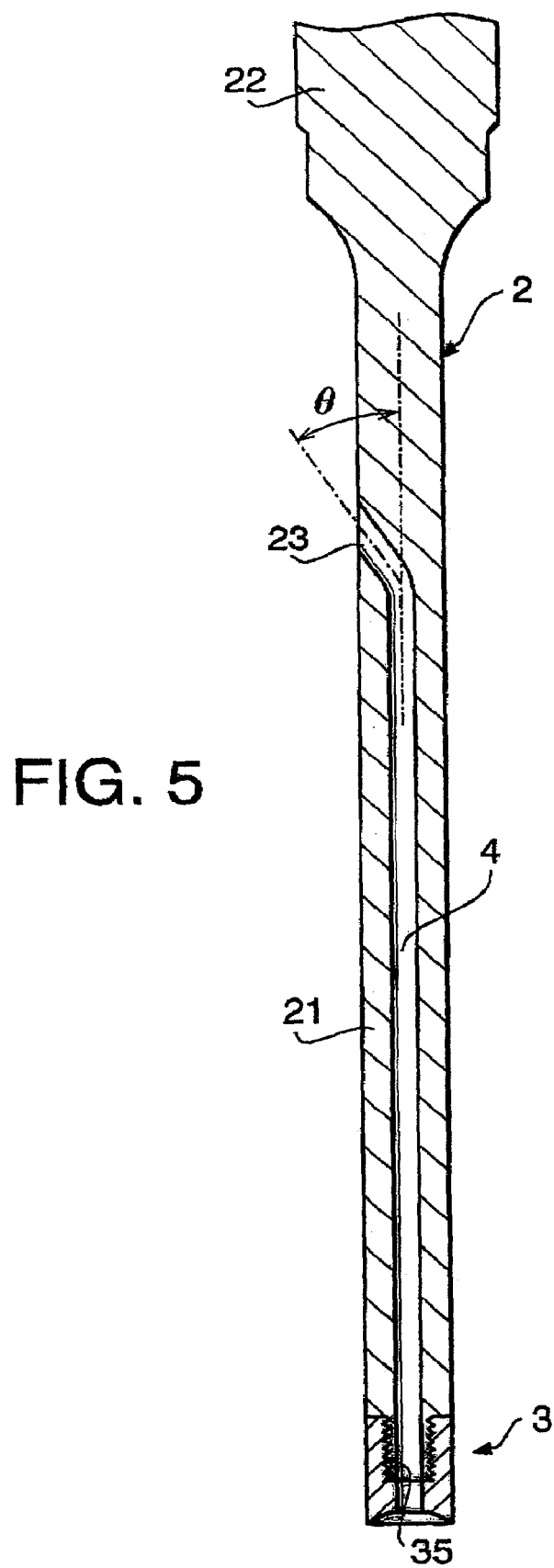
Figure 6:
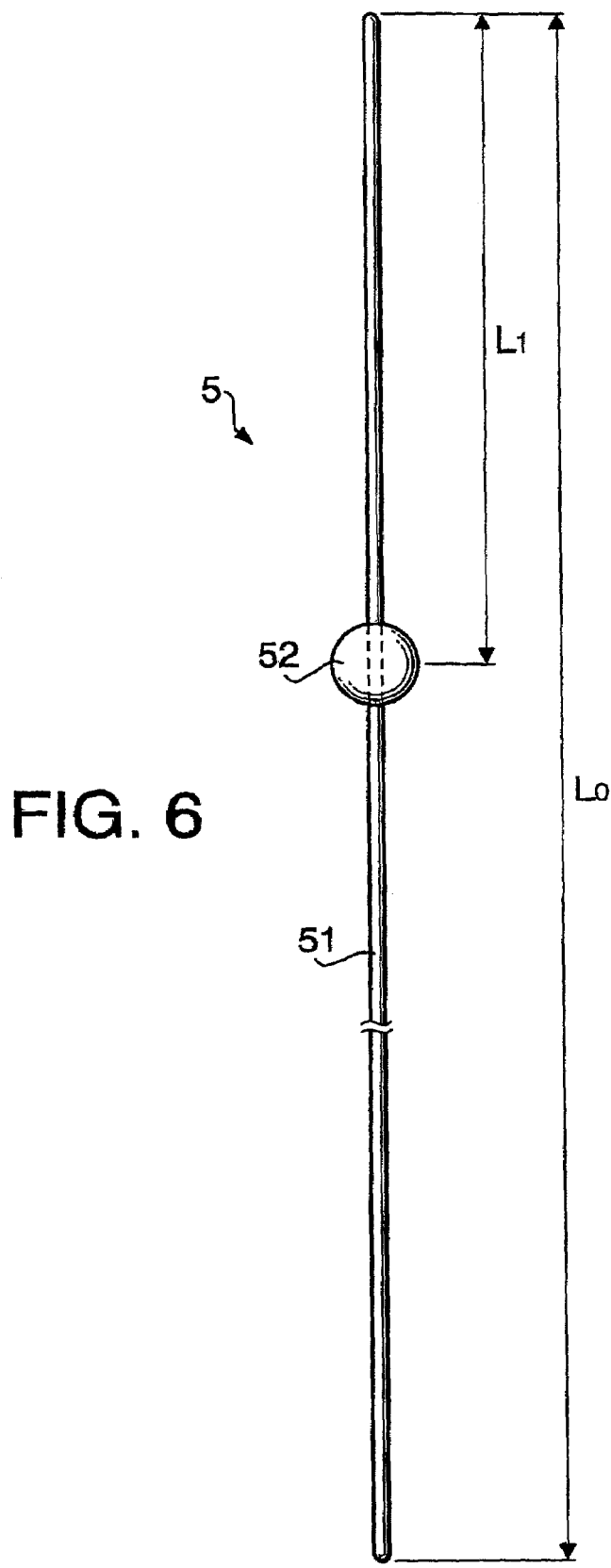
Figure 7:
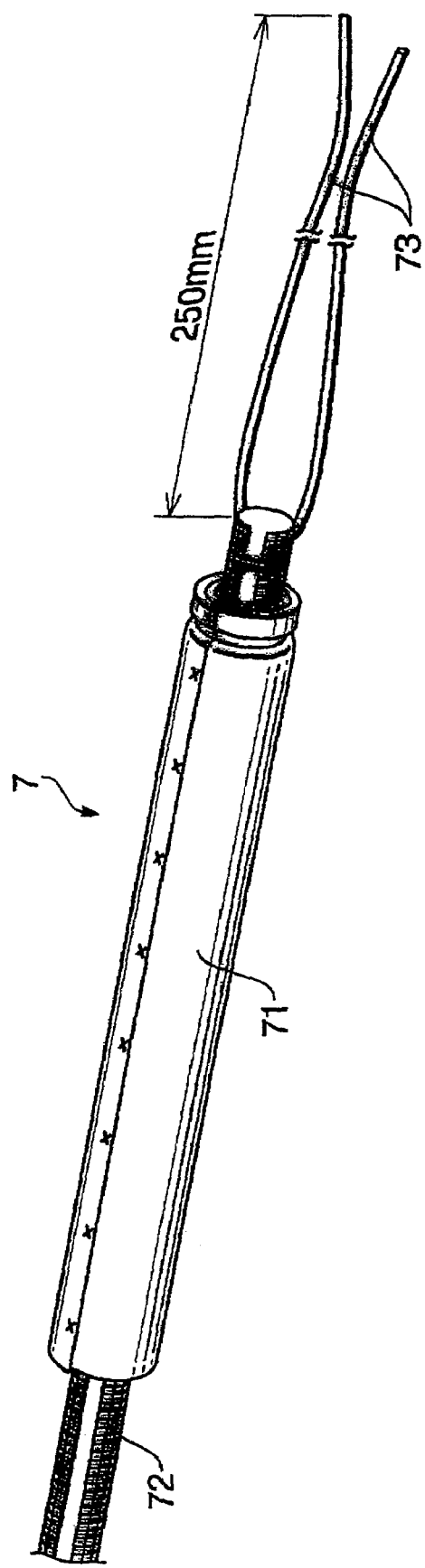

FIG. 3 shows a cross-sectional view of the insertion portion and the pressing member of the surgical instrument of FIG. 1 taken along line A—A, FIG. 4 shows a cross section of the pressing member taken along the center axis thereof, FIG. 5 shows a cross section of the insertion portion and the pressing member of the surgical instrument according to another embodiment of the invention, FIG. 6 shows a side view of the guide wire that is to be used with the surgical instrument shown in FIG. 1, FIG. 7 shows a perspective view of an example of a reconstruction ligament, FIGS. 8 through 19 illustrate the surgical procedure of an anterior cruciate ligament reconstruction using the surgical instrument of FIG. 1.

DETAILED DESCRIPTION OF THE EMBODIMENTS

Hereinafter, a surgical instrument according to an embodiment of the invention will be described with reference to the accompanying drawings.

FIG. 1 is a side view of the surgical instrument 1, or a driving-instrument, according to the embodiment of the invention, and FIG. 2 is a side view of a bone plug 10 that is to be driven into a hole formed in a bone, or a bone tunnel, by the surgical instrument 1 shown in FIG. 1.

The bone plug 10 is to be driven into a bone tunnel together with an artificial ligament so that the ligament is fixed to the bone, as will be described later.

The bone plug 10 has a substantially cylindrical shape with a round proximal end 10a and a distal end 10b having a substantially conical shape with its top portion being cut away. A through hole 11 is formed along the center axis of the bone plug 10, and a plurality of circumferential grooves 12 are formed on the outer surface of the bone plug 10 spaced apart from each other, preferably at a constant distance along the center axis.

The bone plug 10 is preferably made from materials having bio-compatibility. Examples of such materials are calcium phosphate compounds, titanium, titanium alloy, stainless steel, alumina, zirconia, polylactic acid, and polydioxan. Examples of calcium phosphate compounds include tricalcium phosphate, teracalcium phosphate, and apatites such as hydroxyapatite (HAp) and fluorapatite.

The surgical instrument 1 shown in FIG. 1 is utilized for driving the bone plug 10 into the bone tunnel. The surgical instrument 1 is provided with a rod shaped elongated body 2 and a pressing member 3 attached to the distal end of the body 2 to press and thereby drive the bone plug 10 into the bone tunnel.

The proximal side of the body 2 is a grip portion 22 having an outer peripheral surface with small bumps and dips for preventing hands gripping thereon from slipping. The distal side of the body 2 is an insertion portion 21 that is to be inserted into the body of a patient.

The body 2 of the surgical instrument 1 may be made from metals such as stainless steel or other iron alloys, copper, aluminum, titanium, or their alloys. The body 2 may also be made from resins such as ABS resin, polycarbonate, poly-methyl-methacrylate, poly-acetal, poly-phenylene-sulfide resin, and fluorine resin.

FIG. 3 shows a cross-sectional view of the insertion portion 21 and the pressing member 3 attached to the distal end thereof taken along their center axis A. A first guiding hole 4 for guiding a guide wire 5, which will be described later, is formed along the center axis A of the insertion portion 21.

The pressing member 3 is mounted to the distal end of the insertion portion 21 by being screwed at its proximal end into the first guiding hole 4. A second guiding hole 35 is drilled through the pressing member 3 along the center axis thereof, which is in communication with the first guiding hole 4 as the pressing member 3 is mounted to the insertion portion 21.

Preferably, the inner circumferential surfaces of the first and second guiding hole 4 and 35 form one continuous hole, when the pressing member 3 is attached to the insertion portion 21, with a smooth surface without having any steps therebetween so that the guide wire 5 can smoothly move between the first and second guiding hole 4 and 35.

The proximal end portion of the first guiding hole 4 is inclined against the center axis A of the insertion portion 21 at an angle θ and forms an opening 23 at the outer peripheral surface of the insertion portion 21. The angle θ is preferably an acute angle within a range of from 5° to 75°, more preferably from 12° to 60°, and further preferably from 20° to 45°.

As will be described later, the guide wire 5 is inserted into the guiding hole 4 with one of its ends extending out from the opening 23. Due to the acute angle of the end portion of the first guiding hole 4 against the center axis A as described above, the end portion of the guide wire 5 extending out from the opening 23 does not incline towards the distal end of the insertion portion 21, and therefore neither interfere with the sight of the surgeon, nor hinders the operation.

Each of the inner diameters of the first and second guiding holes 4 and 35 is preferably between 1.0 to 5.0 mm, and more preferably between 2.0 to 2.5 mm. It should be noted, however, the inner diameters of the first and second guiding holes 4, and 35 are not limited to the sizes above.

The inner surfaces of the first and second guiding holes 4 and 35, as well as the surface of the guide wire 5, may be treated or coated with materials that decrease friction. Examples of such materials include fluorinated-ethylene-propylene copolymer such as poly-tetra-fluoro-ethylene.

FIG. 4 shows a cross section of the pressing member 3 taken along the center axis thereof. An external thread 31 is formed on the outer peripheral surface of the proximal side portion of the pressing member 3. The pressing member 3 is fixed to the distal end of the inserting portion 21 by screw coupling the external thread 31 with an internal thread formed on the inner circumferential surface of the first guiding hole 4. It should be noted, however, that the pressing member 3 may be detachably mounted by any other suitable means. For example, alternative to screw coupling, the proximal end of the pressing member 3 may be fitted into the guiding hole 4. The pressing member 3 may also be fixed permanently, or formed integrally with the insertion portion 21.

The distal side portion 32 of the pressing member 3 has a larger diameter than the proximal side portion, and a recess 33 having a concave surface 34 is formed on the distal end thereof. The concave surface 34 is formed such that the round proximal end 10a of the bone plug 10 is stably received therein in a right attitude during the driving.

The second guiding hole 35 is drilled through the pressing member 3 from the proximal end to the recess 33. Thus, the recess 33 is in communication with the first guiding hole 4 of the body 2 when the pressing member 3 is mounted to the distal end of the insertion portion 21.

FIG. 5 shows a cross section of the insertion portion 21 and the pressing member 3 according to another embodiment of the invention. The pressing member 3 shown in FIG. 5 has a diameter same as that of the inserting portion 21. The pressing member 3 is mounted to the inserting portion 21 by screwing the distal end of the inserting portion 21 into the second guiding hole 35 of the pressing member 3. Thus, the shape and size of the pressing member 3 (the distal side portion 32) may be widely varied, and the diameter of the pressing member 3 (the distal side portion 32) may also be same as that of the insertion portion 21. Preferably a plurality of pressing members 3, each having different shape and size for the distal side portion 32, is provided and the surgeon selects the most appropriate one, according to the type of operation, and mount it to the insertion portion 21.

The whole pressing member 3, or a part of the pressing member 3 including the concave surface 34, for example, may be made from same materials as those described above for the body 2. Preferably, the whole or a part of the pressing member 3 is made from poly-tetrafluoroethylene or silicon resin to prevent serious damage to the bone plug 10.

FIG. 6 shows a side view of the guide wire 5 that is to be used with the surgical instrument 1 shown in FIG. 1 to drive the bone plug 10 into the bone tunnel.

The guide wire 5 includes a wire 51 and a stopper 52 fixed to a predetermined location of the wire 51. The wire 51 may be a single wire or a bundle of wires and may be made from metal such as stainless steel or titanium alloy, for example.

The wire 51 may be ($L_0$=)400–1000 mm long, preferably ($L_0$=)500–800 mm long, and have a diameter of 0.1–2.0 mm.

The stopper 52 may have various kinds of shapes including semi-sphere, disc, and rod like shapes. In the present embodiment, the stopper has a spherical shape. The diameter of the spherical stopper 52 is larger than the diameter of the first guiding hole 4 formed in the insertion portion 21 of the body 2 so that the stopper 52 does not go into the first guiding hole 4.

The stopper 52 is fixed to the wire 51 by press fitting, caulking, welding, or bonding, for example, at a location that preferably satisfies $L_1$=0.1×$L_0$~0.9×$L_0$, and more preferably, $L_1$=0.6×$L_0$~0.8×$L_0$, where $L_0$ represents the entire length of the wire 51 and $L_1$ represents the distance from the proximal end of the wire 51 to the location the stopper 52 is fixed. It should be noted, however, the location where the stopper 52 is fixed is not limited to that described above. If the stopper is fixed at a location that satisfies $L_1$=0.5×$L_0$, for example, the portion of the wire extending out from the opening hangs down from the surgical instrument and thus does not come into the sight of the surgeon.

The stopper 52 may be made from same materials as those described above for the body 2. The stopper 52 is preferably made from fluoro resin, such as poly-tetrafluoroethylene, silicon resin, or ceramics including calcium phosphate compounds such as hydroxyapatite (HAp).

Hereinafter, an example of an anterior cruciate ligament reconstruction surgical procedure using the surgical instrument 1 of FIG. 1 will be described with reference to FIGS. 7 through 19.

1. First, a reconstruction ligament 7 is provided that includes a fascia lata 71 and a reinforcement mesh 72 such as Leeds-Keio reinforcement mesh, as shown in FIG. 7. A wire is placed through one of the ends of the reconstruction ligament 7 and then folded to form a double wire 73. The double wire 73 is approximately 250 mm long.

Figure 8:
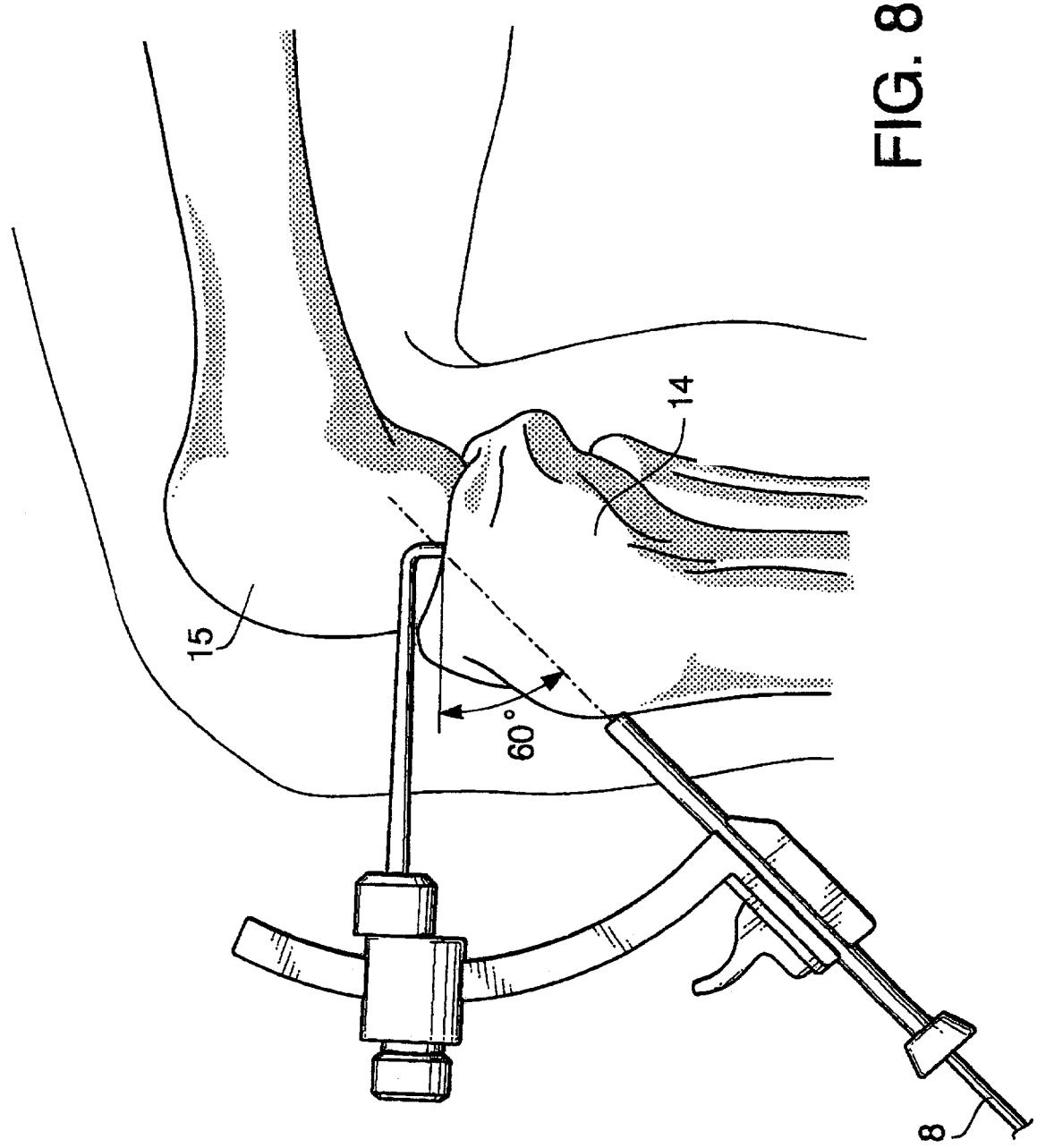
Figure 9:
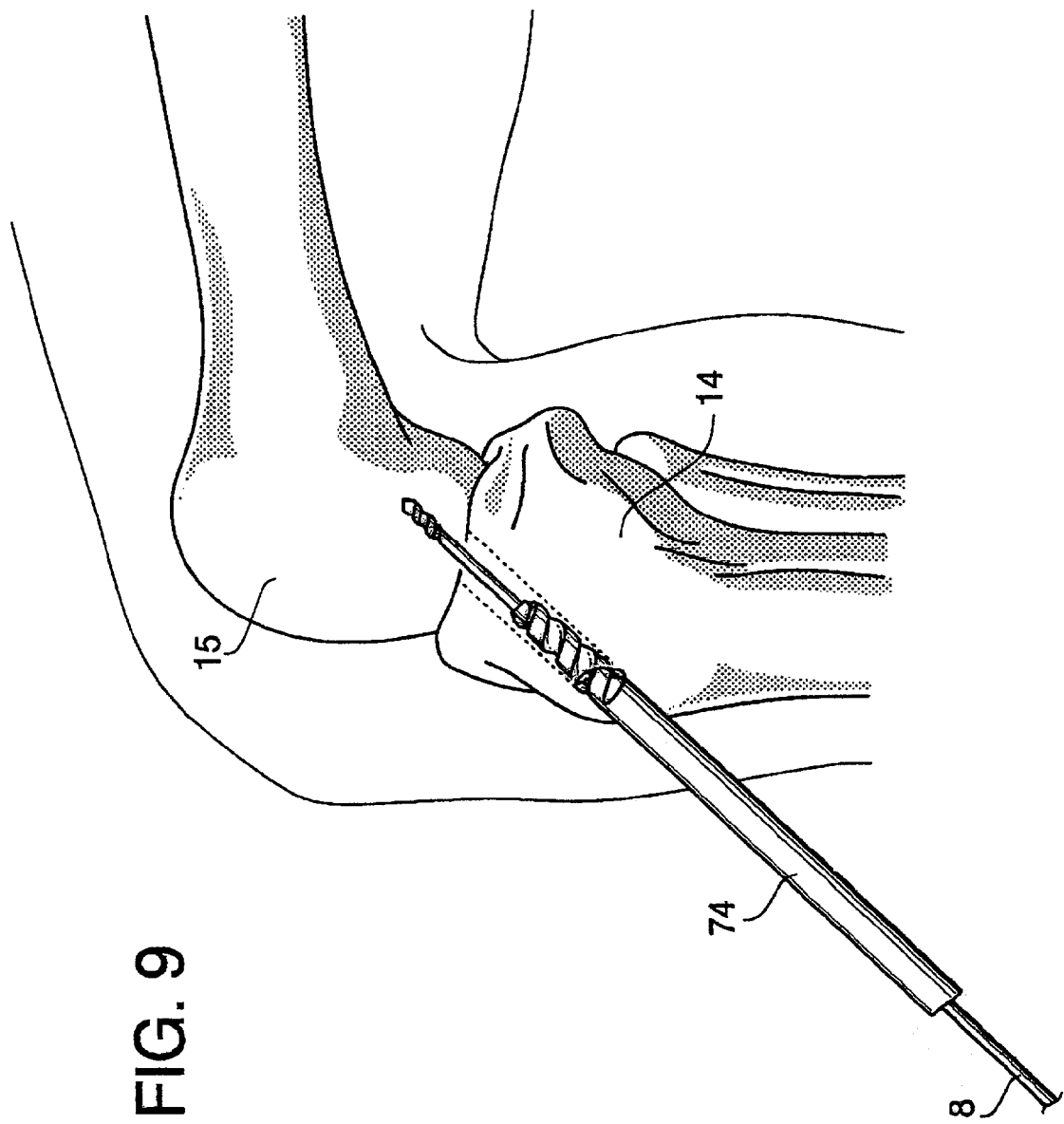

2. Next, as shown in FIG. 8, drill tip guide wire 8 is drilled into the tibia 14 using a tibia drill guide. In this step, the drill tip guide wire 8 is inclined against the articular surface at an angle of 60° and protrudes from the tibia into the joint at a location on the center axis of the bone marrow.

3. Then, a cannulated drill 74 is attached to the drill tip guide wire 8 for drilling a bone tunnel, of which diameter is 10 mm, in the tibia 14 as shown by dotted lines in FIG. 9.

Figure 10:
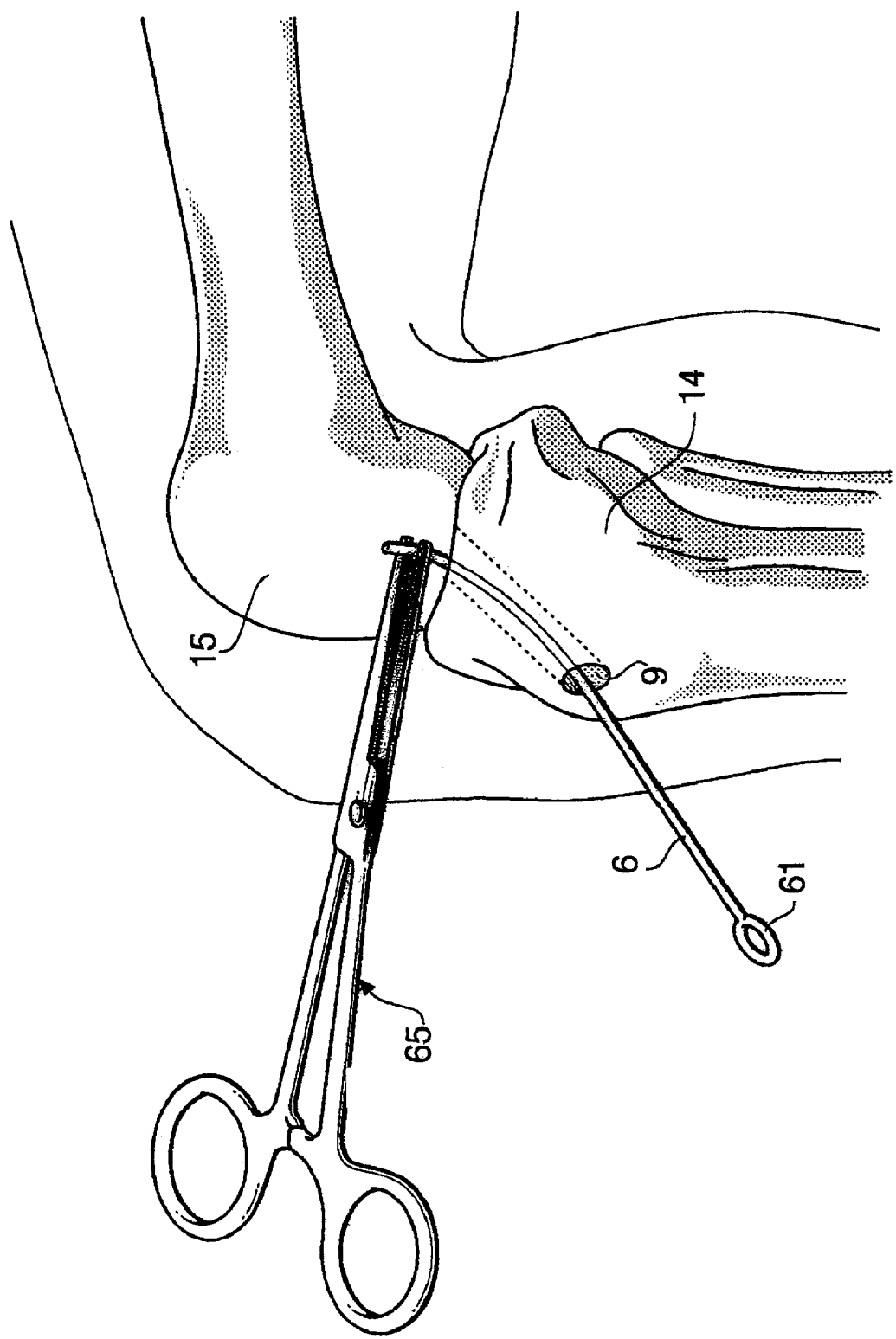
Figure 11:
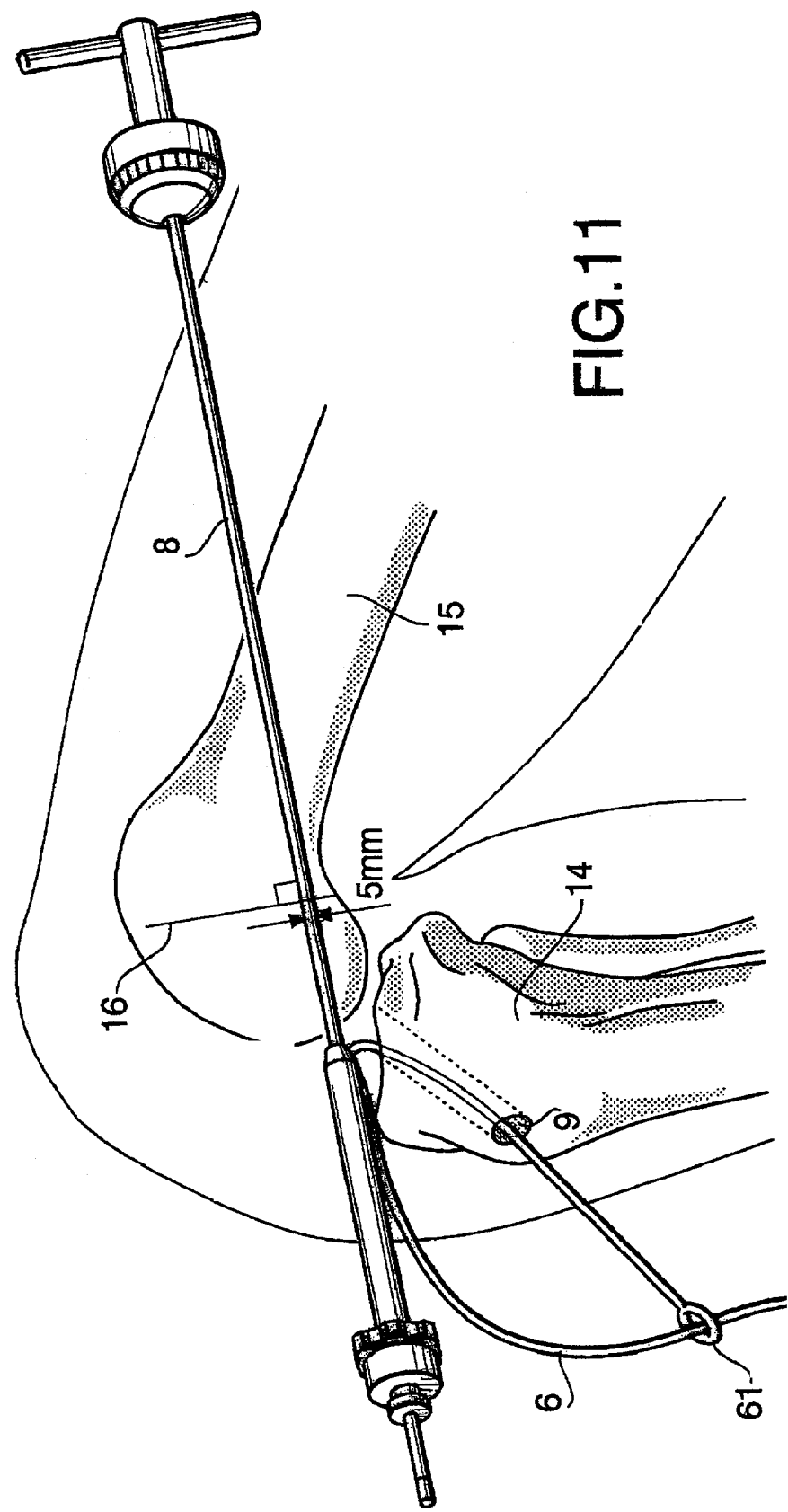

4. Referring now to FIG. 10, a wire 6 having loop 61 at one end thereof is provided. The other end of the wire 6, having no loop, is inserted into the knee joint through the bone tunnel of the tibia 14 and brought out from the anteromedial portal using a forceps 65.

5. Now referring to FIG. 11, the knee is then flexed at 100°–120° and an precise image of the knee joint is obtained using an image intensifier. While observing the image obtained by the image intensifier, the drill tip guide wire 8 is inserted into the knee joint from the anteromedial porta such that the tip of the drill tip guide wire 8 is located perpendicularly against the Blumensaat's line 16 at a location 5 mm away from the intersection of Blumensaat's line and the back end of the femur condyle. Then the drill tip guide wire 8 is penetrated through the femur 15, the quadriceps femoris muscle, and the subcutaneous tissue until the tip protrudes from the front of the thigh.

Figure 12:
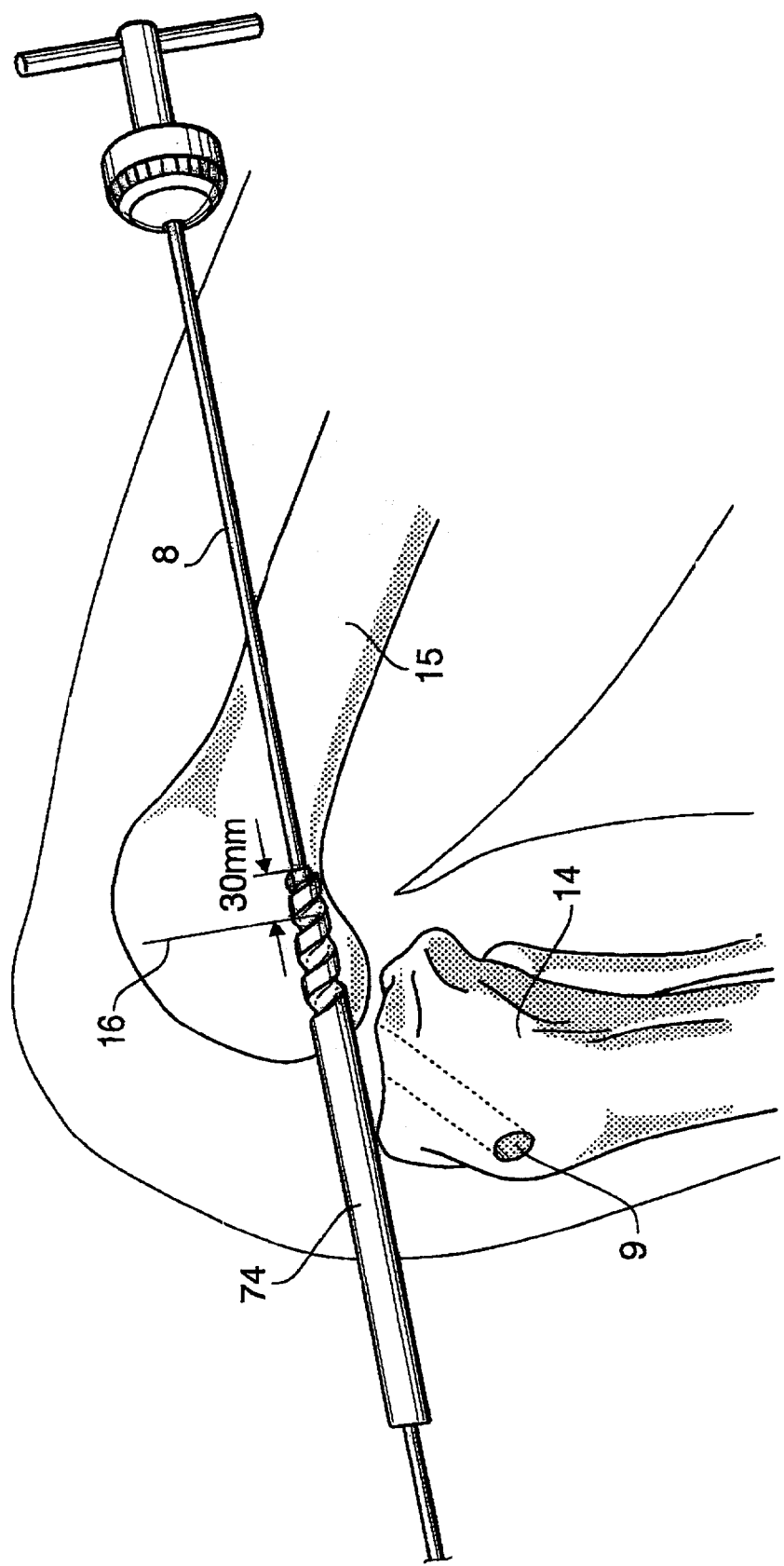
Figure 13:
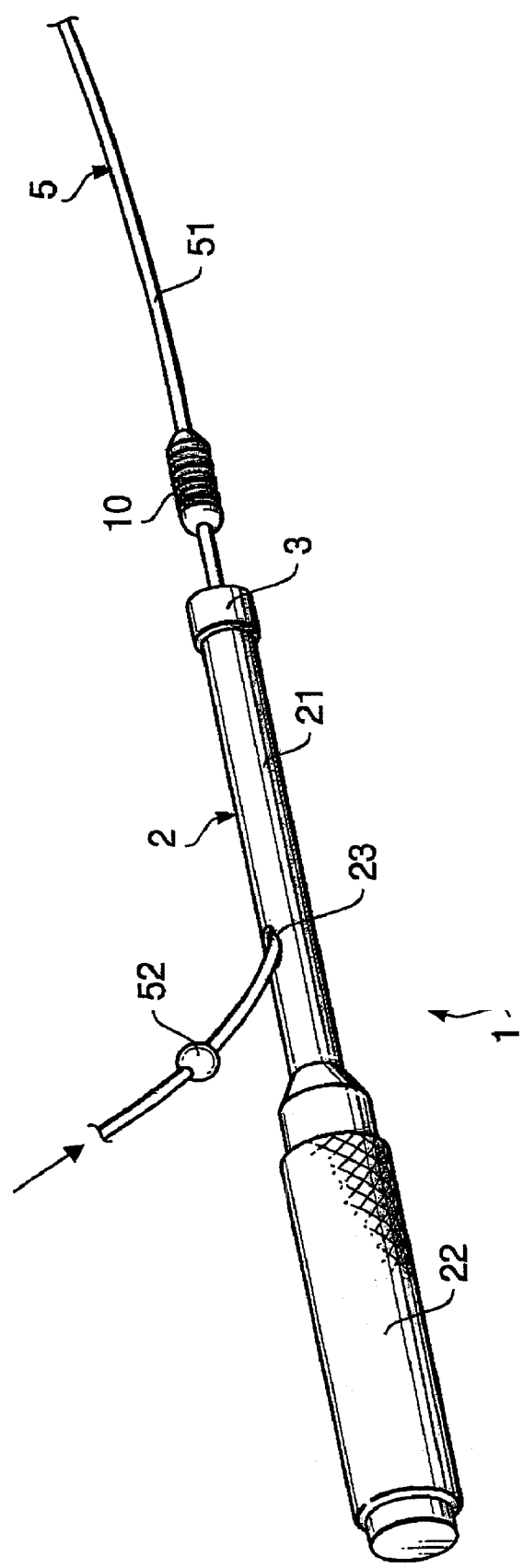

6. The cannulated drill 74 is then mounted to the drill tip guide wire 8, as shown in FIG. 12, and a bone tunnel, 30 mm long and 10 mm in diameter, is drilled in the femur 15 by the cannulated drill 74 while monitoring the femur 15 by the image intensifier.

7. Now referring to FIG. 12, the guide wire 5 is inserted through the first and second guiding holes 4 and 35 of the surgical instrument 1 from the opening 23. The distal end of the guide wire 5, which protrudes from the second guiding hole 35 of the pressing member 3, is further inserted through the through hole 11 of the bone plug 10 such that the bone plug 10 travels along the guide wire 5 towards the surgical instrument 1 and abuts the concave surface 34 of the pressing member 3 with its round proximal end 10a.

8. Next, the ends of the double wire 73 of the reconstruction ligament 7 (see FIG. 7) are connected to the loop 61 of the wire 6 (see FIG. 11). The wire 6 is then pulled so that the ends of the double wire 73 are inserted through the bone tunnel formed in the tibia 14 and brought out from the anteromedial portal. Then, the ends of the double wire 73 are secured to a slit provided at the end of the drill tip guide wire 8. Further, the tip of the guide wire 5, that is passed through the first and second guiding holes 4 and 35 of the surgical instrument 1, is also secured to the slit at the end of the drill tip guide wire 8.

Figure 14:
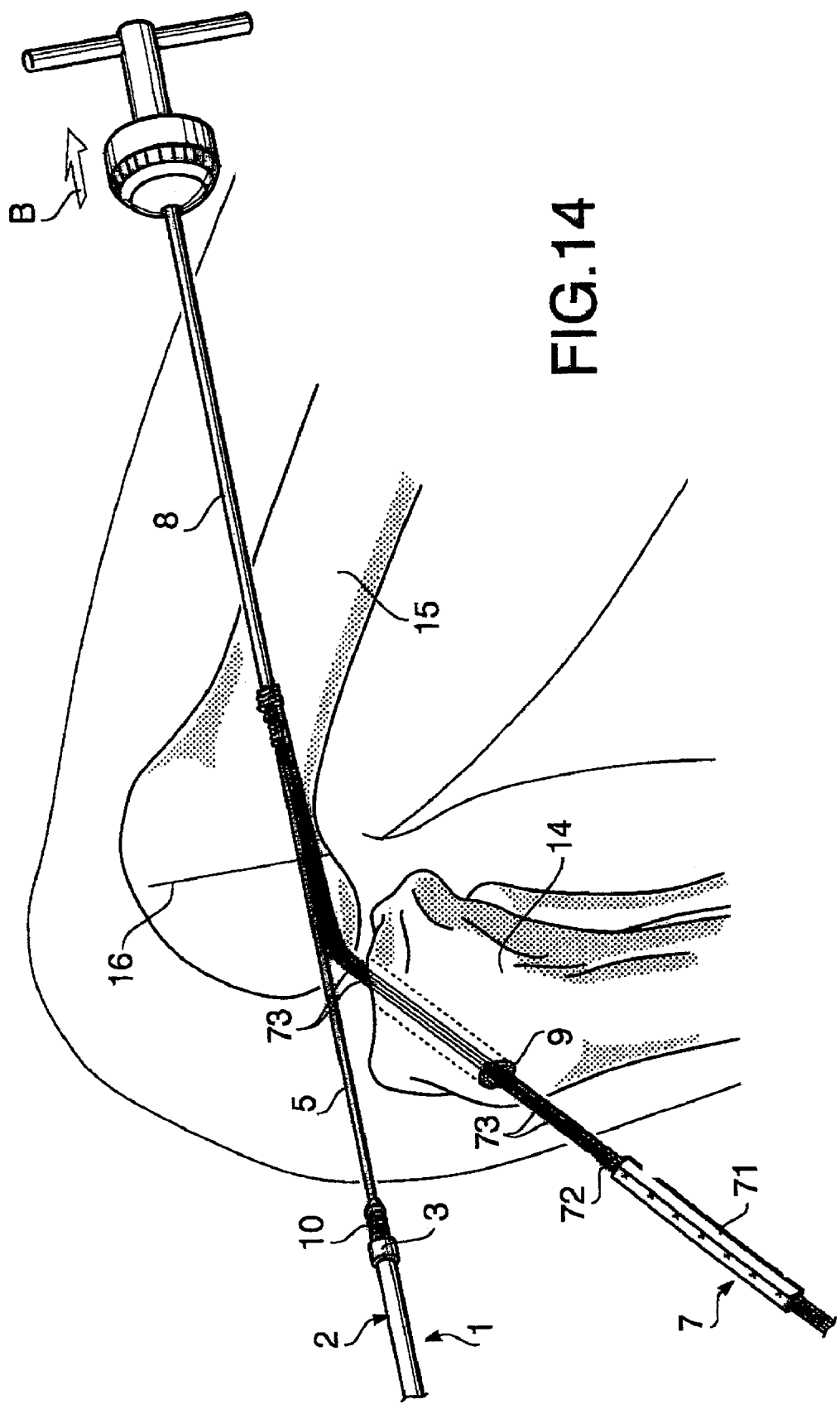

As shown FIG. 14, the drill tip guide wire 8 is then pulled in the direction indicated by the arrow B in FIG. 14, so that both of the two wires 5 and 73 secured to the slit of the drill tip guide wire 8 is pulled out from the thigh after passing through the femur bone tunnel, the quadriceps femoris, and the subcutaneous tissue. Thereafter, the drill tip guide wire 8 is detached from the two wires 5 and 73.

Figure 15:
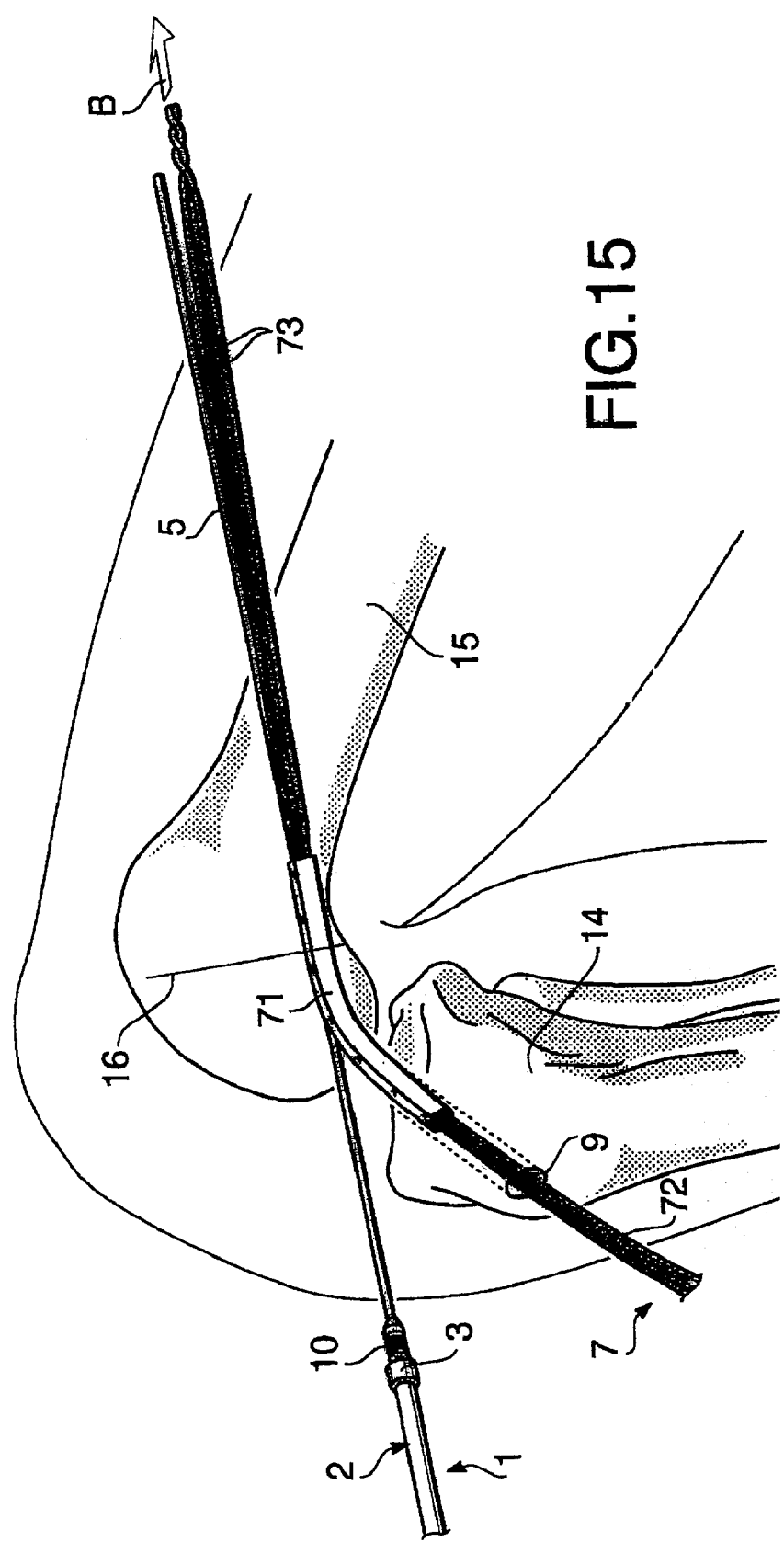

9. Referring to FIG. 15, the double wire 73 is then pulled in the direction of the arrow B to pull the reconstruction ligament 7 into the femur bone tunnel. The position of the double wire 73 is monitored by the image intensifier to confirm that the ligament 7 is inserted into the bone tunnel for a sufficient length.

Figure 16:
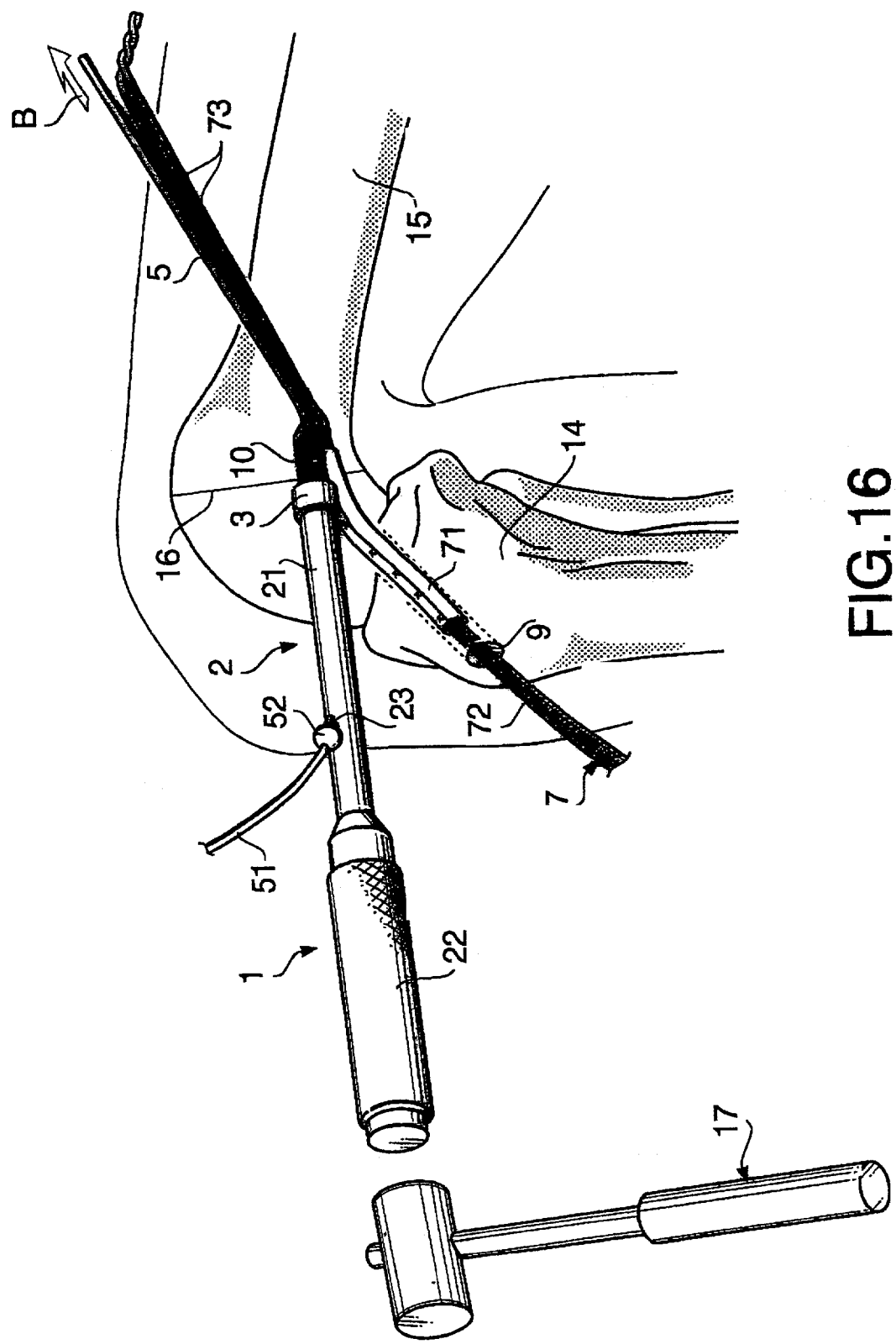

10. Next, the guide wire 5 is pulled in the direction of the arrow B as shown in FIG. 16. Since the stopper 52 fixed to the guide wire 5 has a diameter larger than that of the opening 23 of the surgical instrument 1, the stopper 52 abuts the surgical instrument 1 around the opening 23 as the guide wire 5 is pulled. As a result, the surgical instrument 1 advances together with the guide wire 5 into the knee and towards the bone tunnel. While advancing, the surgical instrument 1 receives the proximal end 10a of the bone plug 10 at the recess 33 of the pressing member 3 since the guide wire 5, which is extending out from the second guiding hole 35 of the pressing member 3, is passed through the through hole 11 of the bone plug 10 and guides the bone plug 10 towards the concave surface 34 of the recess 33. Thus, as the guide wire 5 is pulled, the surgical instrument 1 securely holds and pushes the proximal end 10a of the bone plug 10 by the pressing member 3 and thereby delivers the bone plug 10 into the knee. Note also that the guide wire 5 keeps the distal end lob of the bone plug 10 to be directed towards the bone tunnel and thereby assures a smooth insert of the bone plug 10 into the bone tunnel.

11. Now referring to FIG. 16, the guide wire 5 is pulled until the tip of the bone plug 10 comes to the Blumensaat's line 16. Then, the proximal end of the surgical instrument 1 is hit with a hammer 17, while strongly pulling the guide wire 5, to drive the bone plug 10 into the femur bone tunnel. The location of the bone plug 10 is monitored by the image intensifier, and the bone plug 10 is driven into the femur bone tunnel until the proximal end thereof comes to the Blumensaat's line 16.

Figure 17:
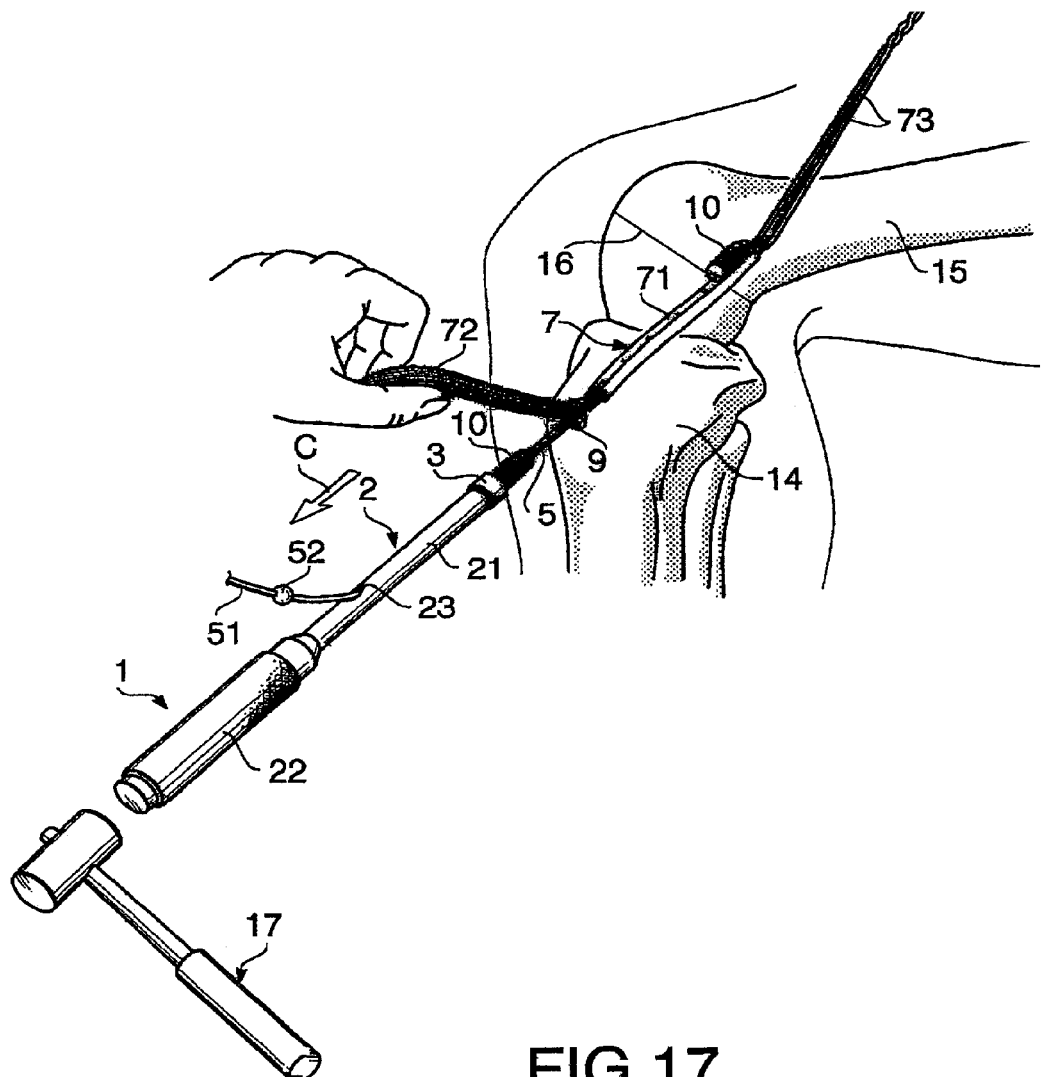

12. Next, the reinforcement mesh 72 is pulled back by hand in the direction indicated by arrow C in FIG. 17 to check whether the bone plug 10 is stably fixed to the femur bone tunnel. If it is confirmed that the bone plug 10 is stably fixed, then the knee joint is flexed at about 40° and the reinforcement mesh 72 of the reconstruction ligament 7 is pulled in a slanting direction, as shown in FIG. 17, so that the next bone plug 10 can be inserted.

Then, the next bone plug 10 is driven into the tibia bone tunnel using the surgical instrument 1, the guide wire 5 and the hammer 17, in the same manner as the bone plug 10 is driven into the femur bone tunnel. During the operation, the location of the bone plug 10 is monitored by the image intensifier so that the bone plug 10 does not protrude into the knee joint.

Figure 18:
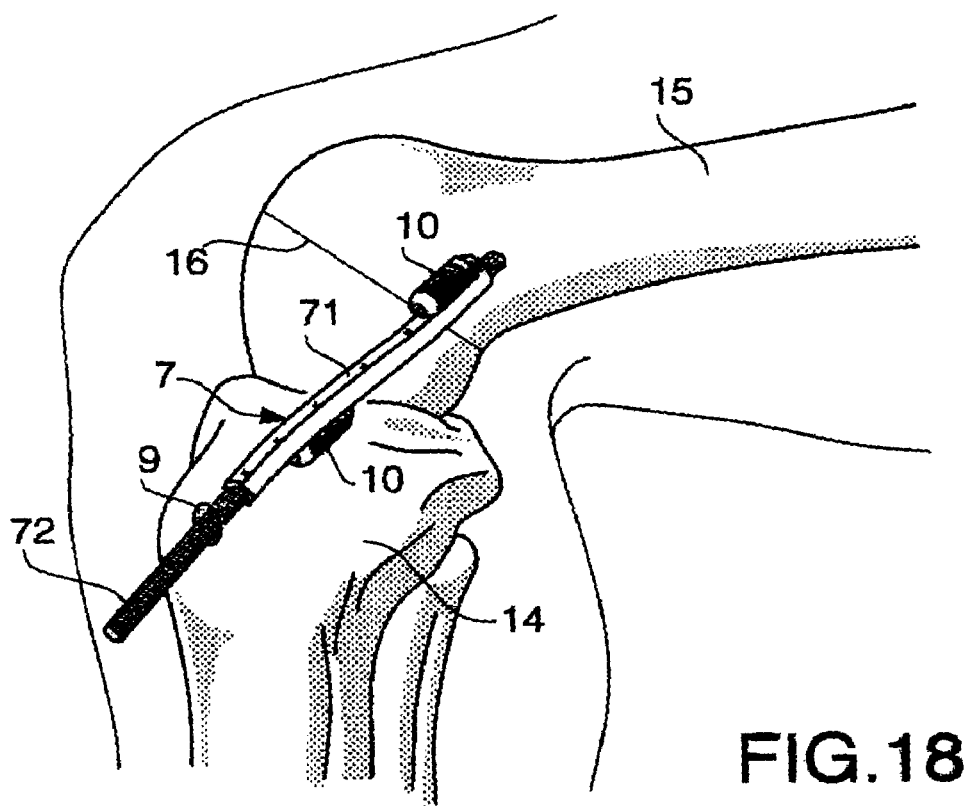

13. After the bone plug 10 is driven into the tibia bone tunnel, the double wire 73 of the reconstruction ligament 7 is pulled out and removed from the knee, as shown in FIG. 18.

Figure 19:
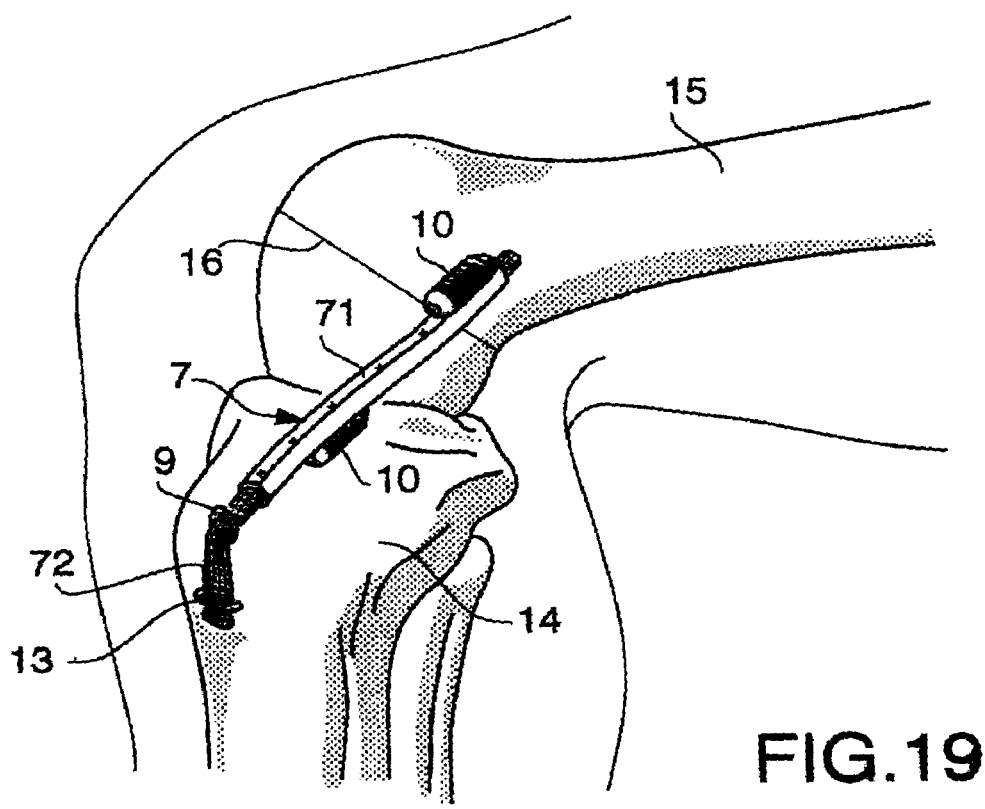

14. Next, the reconstruction ligament 7 is bent, as shown in FIG. 19, such that it covers the entrance 9 of the tibia bone tunnel, and then is fixed to bone cortex of the tibia 14 by means of staple 13, for example. Then, the ligament 7 extending beyond the staple 13 is cut and removed.

Although this invention has been shown and described with respect to a detailed embodiment thereof, it will be understood by those skilled in the art that various changes may be made without departing from the spirit and scope of the invention.

The present disclosure relates to the subject matter contained in Japanese Patent Application No. P2001-114426, filed on Apr. 12, 2001, which is expressly incorporated herein by reference in its entirety.

What is claimed is:

1. A surgical instrument, comprising:
an elongated body having:
a distal end configured to press and drive a bone plug into a bone tunnel,
a front opening provided at said distal end, and
a guide hole in communication with said front opening and configured so that a guide wire, inserted into said guide hole, extends out of said front opening to guide the bone plug towards said distal end of said elongated body wherein a proximal end portion of the said guide hole is inclined with respect to a longitudinal axis of said elongated body at an acute angle to form a side opening at an outer peripheral surface of said elongated body,
wherein said distal end includes a pressing member having a distal side portion and a proximal side portion, said distal side portion having a larger diameter than said proximal side portion, a recess provided in said pressing member, said recess configured to receive at least a portion of the bone plug, so that pulling of the guide wire that extends out of the front opening, away from the bone plug, pulls the bone plug and the elongated body towards the bone tunnel, and
wherein said front opening is provided in said recess.

2. The surgical instrument according to claim 1, wherein said guide hole extends along a longitudinal axis of said elongated body.

3. The surgical instrument according to claim 1, wherein said recess is configured as a concave surface.

4. The surgical instrument according to claim 1, wherein said guide hole includes a coating for decreasing friction between the guide wire and said guide hole.

5. The surgical instrument according to claim 1, wherein said elongated body includes a grip portion having a rough outer peripheral surface.

6. The surgical instrument according to claim 1, wherein said elongated body includes a body and a detachable portion detachably attached to said body, said detachable portion includes said distal end of said elongated body.

7. The surgical instrument according to claim 1, wherein the guide wire extends through a through hole in the bone plug to guide the bone plug towards said distal end of said elongated body.

8. The surgical instrument according to claim 1, a distal end of the guide wire passing through the bone tunnel, the guide wire including a stopper configured to engage the guide hole and to urge the elongated body such that the distal end of the elongated body is pulled toward the bone tunnel when the distal end of the guide wire is pulled away from the elongated body.

9. In combination, a surgical instrument and a guide wire, said surgical instrument comprising:
a member having an outer peripheral surface,
a distal end configured to press and drive a bone plug into a bone tunnel,
a front opening formed at said distal end,
a side opening formed at said outer peripheral surface, and
a guide hole in communication with said front opening and said side opening,
said guide wire comprising:
a wire insertable into said guide hole from said side opening to extend out of said front opening, a stopper fixed to said wire, said stopper being located outside of said surgical instrument and being larger than either said guiding hole or said side opening, and
wherein pulling of the guide wire that extends out of the front opening, away from the bone plug, pulls the bone plug and the elongated body towards the bone tunnel,
wherein said distal end of said surgical instrument includes a recess configured to receive a proximal end of the bone plug,
wherein said front opening is provided in said recess.

10. The combination according to claim 9, wherein said stopper is configured to have a shape that is not insertable into said guiding hole.

11. The combination according to claim 10, wherein said stopper comprises a sphere having a diameter larger than a diameter of said side opening.

12. The combination according to claim 9, wherein said wire includes a coating for decreasing friction between said wire and said guide hole.

13. The combination according to claim 9, wherein said recess comprises a concave surface.

14. The combination according to claim 9, wherein said surgical instrument has an elongated shape,
a proximal end portion of said guide hole is inclined with respect to a longitudinal axis of said elongated shape at an acute angle to form said side opening.

15. The combination according to claim 9, wherein said guide hole includes a coating for decreasing friction between said guiding hole and said guide wire.

16. The combination according to claim 9, wherein said surgical instrument includes a grip portion having a rough outer peripheral surface.

17. The combination according to claim 9, wherein said surgical instrument includes a body and a detachable portion detachably attached to said body, said detachable portion includes said distal end of said surgical instrument.

18. The combination according to claim 9, wherein said wire extends through a through hole in the bone plug to guide the bone plug towards said distal end of said surgical instrument.

19. The combination according to claim 9, a distal end of the guide wire passing through the bone tunnel, the stopper configured to engage the guide hole and to urge the elongated body such that the distal end of the elongated body is pulled toward the bone tunnel when the distal end of the guide wire is pulled away from the elongated body.

20. A surgical instrument, comprising:
- an elongated body having:
  - a distal end configured to press and drive a bone plug into a bone tunnel,
  - a front opening provided at said distal end,
  - a guide hole in communication with said front opening and configured so that a guide wire, inserted into said guide hole, extends out of said front opening to guide the bone plug towards said distal end of said elongated body,
  - wherein a proximal end portion of said guide hole is inclined with respect to a longitudinal axis of said elongated body at an acute angle to form a side opening at an outer peripheral surface of said elongated body, and
  - wherein said distal end includes a pressing member having a distal side portion and a proximal side portion, said distal side portion having a larger diameter than said proximal side portion, and a recess provided in said pressing member, said recess configured to receive at least a portion of the bone plug within said recess, said front opening being provided in said recess.

21. The surgical instrument according to claim 20, wherein said recess is configured as a concave surface.

22. The surgical instrument according to claim 20, wherein said guide hole includes a coating for decreasing friction between the guide wire and said guide hole.

23. The surgical instrument according to claim 20, wherein said elongated body includes a grip portion having a rough outer peripheral surface.

* * * * *